United States Patent [19]

Mizutani et al.

[11] Patent Number: 5,874,229
[45] Date of Patent: Feb. 23, 1999

[54] METHOD FOR AVOIDING INFLUENCE OF HEMOGLOBIN

[75] Inventors: Satoru Mizutani; Hiroshi Tamura; Susumu Nishino, all of Kyoto, Japan

[73] Assignee: Kyoto Daiichi Kagaku Co., Ltd., Kyoto, Japan

[21] Appl. No.: 686,918

[22] Filed: Aug. 1, 1996

[30] Foreign Application Priority Data

Aug. 7, 1995 [JP] Japan ................................ 7-231909

[51] Int. Cl.$^6$ .......................... G01N 33/573; C12Q 1/00; C12Q 1/52; C12Q 1/37
[52] U.S. Cl. ................... 435/7.4; 435/4; 435/16; 435/15; 435/23; 435/24; 435/26; 435/17; 435/962; 435/968; 436/63; 436/800
[58] Field of Search ................... 436/66, 63, 800; 422/56; 435/18, 21, 7.4, 4, 16, 15, 23, 24, 26, 17, 962, 968

[56] References Cited

U.S. PATENT DOCUMENTS

| | | | |
|---|---|---|---|
| 4,451,563 | 5/1984 | Kaufman | 435/21 |
| 4,681,841 | 7/1987 | Matsumoto et al. | 435/18 |
| 4,803,159 | 2/1989 | Smith-Lewis | 435/26 |
| 4,970,171 | 11/1990 | Messenger et al. | 436/66 |
| 5,077,011 | 12/1991 | Amano et al. | 422/56 |
| 5,096,812 | 3/1992 | Rachel et al. | 435/24 |
| 5,331,958 | 7/1994 | Oppenheimer | 128/633 |

FOREIGN PATENT DOCUMENTS

| | | |
|---|---|---|
| 0279988 | 8/1988 | European Pat. Off. |
| 3222707 | 12/1982 | Germany . |
| 60-263858 | 12/1985 | Japan . |

OTHER PUBLICATIONS

Shahangian et al, *Journal of Analytical Toxicology*, 8:273–276 (1984).
Fossati et al, *Clin. Chem.*, 26(2):227–231 (1980).

*Primary Examiner*—Louise N. Leary
*Attorney, Agent, or Firm*—Sughrue, Mion, Zinn, Macpeak & Seas, PLLC

[57] ABSTRACT

A method for avoiding influence of hemoglobin, in which the influence is caused by the changes with time in the absorption wavelength of hemoglobin when light absorption of a color reaction of a sample is measured by a rate assay, wherein the method comprises measuring the light absorption at a wavelength of from 517 to 529 nm or from 580 to 592 nm.

3 Claims, 2 Drawing Sheets

METHOD FOR AVOIDING INFLUENCE OF HEMOGLOBIN

FIELD ON THE INVENTION

The present invention relates to a method for avoiding influence (interference) of hemoglobin when light absorption of a color reaction is measured by a rate assay.

BACKGROUND OF THE INVENTION

In carrying out biochemical assays and biochemical measurements in clinical tests, there are two methods: one is a method using liquid reagents, and the other is a method using dry reagents (referred to as "dry assay elements"). In both methods, coloration of a reaction system is observed for detection or determination by using light reflectance. Particularly, a rate assay (a method measuring changed amounts at two or more points and the concentration is calculated from the obtained reaction rate) is an assay method generally used for the light absorption measurement using dry assay elements.

In such a method, hemocytes are separated and removed from whole blood and the resulting plasma or serum is used as a sample to be tested. However, the plasma or serum sample is sometimes contaminated by hemoglobin when the sample is prepared from whole blood in which hemolysis of erythrocytes occurred before or during the separation step. As a consequence, the data obtained by this assay become greatly different from the actual data, because the data of the desired component are overlapped with those of hemoglobin (so-called "fogging") and the absorption of hemoglobin changes with time.

Consequently, it is necessary to avoid influence of the changes with time in the absorption of hemoglobin. Some methods have been proposed for this purpose such as a method measuring a blank, a method denaturing hemoglobin physically or chemically to prevent the changes with time (e.g., JP-B-3-58467, the term "JP-B" as used herein means an "examined Japanese patent publication") and a method measuring light absorption at a wavelength of 650 nm or more at which hemoglobin shows less absorption (e.g., JP-A-62-209360, the term "JP-A" as used herein means an "unexamined published Japanese patent application").

Of these methods, the method measuring a blank requires extra labor because the light absorptions of the blank and sample are measured. Particularly, when dry assay elements are used, the blank measurement is difficult because all reagents to be used are combined in one form.

Also, the method denaturing hemoglobin requires complex handling and may denature the desired component to be assayed (for example, enzyme), so that this method is not suitable for the dry assay element whose advantage is easy and simple handling.

The method measuring light absorption at a wavelength of 650 nm or more at which hemoglobin shows less absorption is effective when liquid reagents are used. That is, although absorption of hemoglobin is slightly detectable at a wavelength of 650 nm or more, the fogging of hemoglobin causes no problem when an excessively diluted sample such as the liquid system is measured at a wavelength of small hemoglobin absorption (for example, 680 nm).

However, when a sample is used in an assay without dilution such as the case of dry assay elements, even a small absorption of hemoglobin at a wavelength of 600 nm or more exerts serious problematic influence upon the measured value.

SUMMARY OF THE INVENTION

Consequently, an object of the present invention is to provide a novel method for avoiding influence of hemoglobin, which is not swayed by the changes with time in the absorption wavelength of hemoglobin and therefore does not cause the aforementioned problems.

This and other objects of the present invention have been attained by a method for avoiding influence of hemoglobin, in which the influence is caused by the changes with time in the absorption wavelength of hemoglobin when light absorption of a color reaction of a sample is measured by a rate assay, wherein the method comprises measuring the light absorption at a wavelength of from 517 to 529 nm or from 580 to 592 nm.

DETAILED DESCRIPTION OF THE INVENTION

Figure 1:
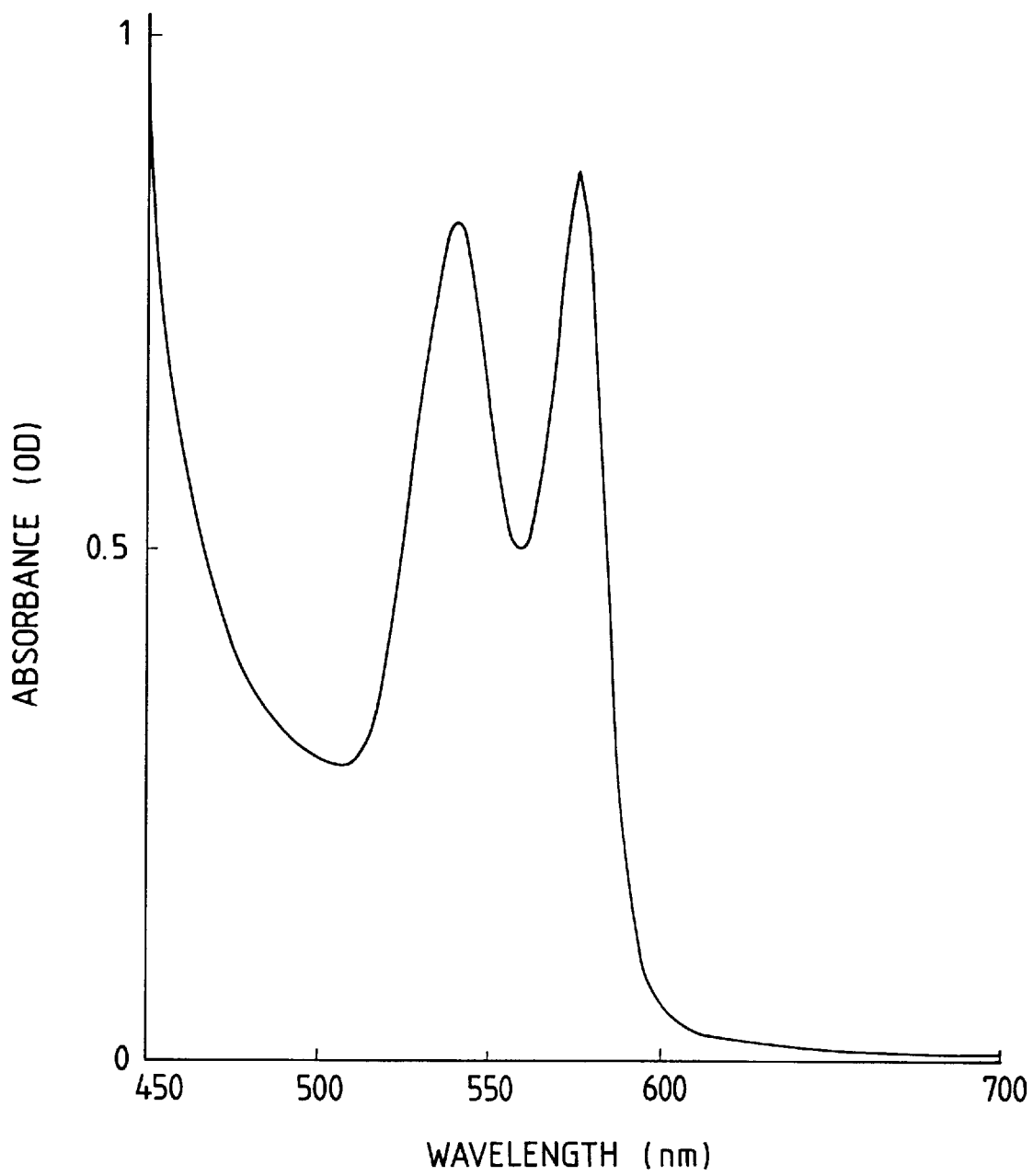
FIG. 1 shows the absorption wavelength of hemoglobin.

In the present invention, the light absorption is preferably measured at a wavelength of from 520 to 526 nm or from 583 to 589 nm.

Furthermore, in the present invention, the sample to be measured is preferably a dry assay element. However, sufficient effects can be obtained if the sample is liquid. Since the changes with time in the light absorption of contaminated hemoglobin can be avoided, the method of the present invention is preferably applied to a rate assay. The rate assay is a method in which amounts of changes at two or more points (reaction rate) are measured. This method is often used with dry assay elements.

Also, in the present invention, the sample to be measured preferably contains a visible coloring agent. The visible coloring agent may be an oxidizing coloring agent or a reducing coloring agent.

Examples of the oxidizing coloring agent for use in the present invention include 3,3',5,5'-tetramethylbenzidine (TMBZ), N-(3-sulfopropyl)-3,3',5,5'-tetramethylbenzidine (TMBZ•PS), N-ethyl-N-(2-hydroxy-3-sulfopropyl)-3-methoxyaniline, sodium salt, dihydrate (ADOS), N-ethyl-N-3-sulfopropyl)-3-methoxyaniline, sodium salt, monohydrate (ADPS), N-ethyl-N-(2-hydroxy-3-sulfopropyl)aniline, sodium salt, monohydrate (ALOS), N-ethyl-N-(3-sulfopropyl)aniline, sodium salt (ALPS), N-ethyl-N-(2-hydroxy-3-sulfopropyl)- 3,5-dimethoxyaniline, sodium salt (DAOS), N-ethyl-N-(3-sulfopropyl)-3,5-dimethoxyaniline, sodium salt, monohydrate (DAPS), N-(3-sulfopropyl) aniline, sodium salt, monohydrate (HALPS), N-(2-hydroxy-3-sulfopropyl)-3,5-dimethoxyaniline, sodium salt (HDAOS), N-(3-sulfopropyl)-3,5-dimethoxyaniline, sodium salt, monohydrate (HDAPS), N-ethyl-N-(2-hydroxy-3-sulfopropyl)-3,5-dimethylaniline, sodium salt, monohydrate (MAOS), N-ethyl-N-(3-sulfopropyl)-3,5-dimethylaniline, sodium salt, monohydrate (MAPS), N-ethyl-N-(2-hydroxy-3-sulfopropyl)-3-methylaniline, sodium salt, dihydrate (TOOS), and N-sulfopropylaniline (HALPS).

Examples of the reducing coloring agent for use in the present invention include tetrazolium salts such as 2-(4-iodophenyl)-3-(4-nitrophenyl)-5-phenyl-2H-tetrazolium chloride (INT), 3-(4,5-dimethyl-2-thiazolyl)-2,5-diphenyl-2H-tetrazolium bromide (MTT), 3,3'-(1,1'-biphenyl-4,4'- diyl)-bis(2,5-diphenyl-21i-tetrazolium chloride) (Neo-TB (Neo-TetrazoliumBlue)), 3,3'-(3,3'-dimethoxy-(1,1'-biphenyl)-4,4'-diyl)-bis(2-(4-nitrophenyl)-5-phenyl-2H-tetrazolium chloride) (Nitro-TB (Nitrotetrazolium Blue)), 3,3'-(3,3'-dimethoxy-(1,1'-biphenyl)-4,4'-diyl)-bis(2,5-diphenyl-2H-tetrazolium chloride) (TB (Tetrazolium Blue)), 2-(4-iodophenyl)-3-(4-nitrophenyl)-5-(2,4-disulfophenyl)-2H-tetrazolium, monosodium salt (WST-1), and 2-(4-iodophenyl)-3-(2,4-dinitrophenyl)-5-(2,4-disulfophenyl)-2H-tetrazolium, monosodium salt (WST-3).

Moreover, the method of the present invention is preferably used for measuring an enzyme activity.

Examples of the enzyme of which activity is measured by the method of the present invention include glutamic-oxaloacetic transaminase (GOT), glutamic-pyruvic transaminase (GPT), lactic dehydrogenase (LDH), lipase, leucine aminopeptidase (LDH), γ-glutamyltransferase (γGTP), creatine phosphokinase (CPK), and pyruvate kinase (PK).

FIG. 1 shows the absorption wavelength of hemoglobin (the absorbance (OD) is plotted as ordinate and the wavelength (nm) as abscissa). Since the absorption of hemoglobin is small at a wavelength of 600 nm or more as shown in FIG. 1, it is generally considered that it does not exert influence upon measured values when measured at the wavelength. However, as described in the foregoing, the absorbance of hemoglobin changes with time and causes an error which is not negligible in the case of dry assay systems.

Figure 2:
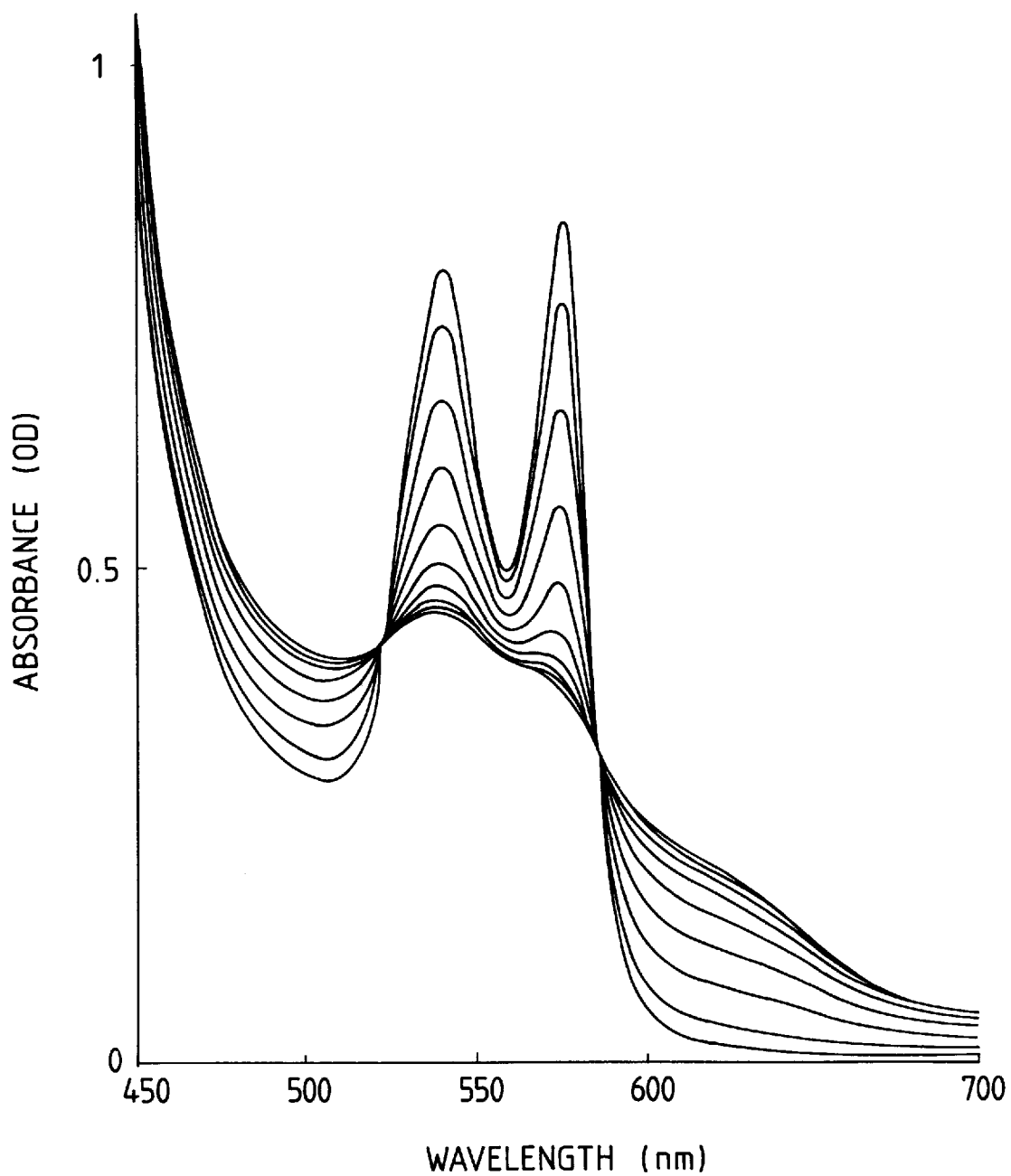
FIG. 2 shows the changes with time in the absorption wavelength of hemoglobin.

An example of the changes with time is shown in FIG. 2. FIG. 2 shows the changes in the absorption of hemoglobin measured at pH 11 (the absorbance (OD) is plotted as ordinate and the wavelength (nm) as abscissa). A space between a line and its adjacent line shows an interval of 1 minute. As shown in FIG. 2, curves become gentle (close to horizontal) with the lapse of time. A reaction reagent whose coloring degree increases with the lapse of time causes a negative error of the measured value at a wavelength of from 520 to 590 nm or a positive error at other visible wavelengths. On the other hand, a reaction reagent whose coloring degree decreases with the lapse of time causes a positive error of the measured value at a wavelength of from 520 to 590 nm or a negative error at other visible wavelengths. Even under milder conditions, these changes occur in more or less degree and cause a positive or negative error of the measured value. This influence is significant in the case of dry assay elements. A principle of the present invention is to carry out the measurement at a wavelength at which these changes with time do not occur.

The wavelength at which periodical changes in the absorption of hemoglobin do not occur is preferably within the range of from 520 to 526 nm or from 583 to 589 nm. However, the range may vary to some extent depending on the measuring conditions such as temperature. The measurement of the present invention is carried out at a temperature of 20° C. to 45° C., preferably at 25° C. or 37° C.

The present invention is now illustrated in greater detail by way of the following examples, but it should be understood that the present invention is not to be construed as being limited thereto.

EXAMPLE 1

Dry Assay Element For Use In The Measurement Of GPT (Glutamic-Pyruvic Transaminase)

Preparation of reagent coating solution:

(Formulation)

| L-Alanine | 0.9 g |
|---|---|
| α-Ketoglutaric acid | 0.1 g |
| Pyruvate oxidase | 20 K units |
| Phosphoric acid | 0.05 g |
| Peroxidase | 10 K units |
| 4-Aminoantipyrine | 0.05 g |
| N-Ethyl-N-(2-hydroxy-3-sulfopropyl)-3,5-dimethoxyaniline sodium salt | 0.05 g |
| Sodium alginate | 2.0 g |
| Distilled water | 8.0 g |
| Potassium dihydrogenphosphate | 0.04 g |
| Disodium hydrogenphosphate | 0.24 g |

The above components were mixed to prepare a reagent coating solution, and the coating solution was coated on an opaque polyethylene terephthalate film to a wet thickness of 200 μm and dried at 40° C. for 30 minutes, thereby obtaining a reagent layer.

Preparation of developing layer:

(Formulation)

| Triton X-100 | 0.10 g |
|---|---|
| Distilled water | 9.90 g |

A piece of polyester cloth having a thickness of 0.25 mm (Savina Minimax, trade name by Kanebo, LTD.) was immersed with a mixture of the above components to obtain a developing layer.

Processing into assay element:

The wet developing layer obtained above was laminated on the previously prepared reagent layer and dried at 40° C. for 30 minutes. The thus obtained laminate was cut to a size of 5 mm×7 mm and, using a pressure sensitive adhesive double coated tape, fixed to a tip of a white polyethylene terephthalate piece having a size of 5 mm×80 mm to obtain an assay element.

Measurement:

A whole blood sample collected from a healthy person was divided into two portions: one was subjected to artificial hemolysis; and the other was not treated. Each of the serum samples prepared therefrom was mixed with 30 units/l of GPT, and a 6 μl portion of the resulting mixture was applied to the assay element and incubated at 37° C. Thereafter, influence of hemoglobin upon measured values was examined by monitoring each reflectance at 575, 585 and 610 nm during a period of from 3 to 4 minutes after commencement of the incubation. Concentration of hemoglobin was measured and confirmed by a reflection absorption meter (SPOTCHEM, trade name by Kyoto Daiichi Kagaku Co., Ltd.) to find that the sample after hemolysis contained 300 mg/dl of hemoglobin.

Reflectances were converted to K/S values in accordance with the formula of Kubelka-Munk to calculate their difference (ΔK/S value). The results are shown in Table 1.

TABLE 1

| Wavelength | Hemoglobin conc. | | Error |
|---|---|---|---|
| | 0 mg/dl | 300 mg/dl | |
| 575 nm | Δ 0.025 | Δ 0.021 | −14% |
| 585 nm | Δ 0.027 | Δ 0.027 | ±0% |
| 610 nm | Δ 0.025 | Δ 0.026 | +4% |

EXAMPLE 2

Dry Assay Element For Use In The Measurement Of GPT Using Other Color-Producing Reagent Preparation of reagent coating solution:

(Formulation)

| | |
|---|---|
| L-Alanine | 0.9 g |
| α-Ketoglutaric acid | 0.1 g |
| Pyruvate oxidase | 20 K units |
| Phosphoric acid | 0.05 g |
| Peroxidase | 10 K units |
| 4-Aminoantipyrine | 0.05 g |
| N-Ethyl-N-(2-hydroxy-3-sulfopropyl)-3,5-dimethoxyaniline sodium salt | 0.05 g |
| Sodium alginate | 2.0 g |
| Distilled water | 8.0 g |
| Potassium dihydrogenphosphate | 0.04 g |
| Disodium hydrogenphosphate | 0.24 g |

The above components were mixed to prepare a reagent coating solution, and the coating solution was coated on an opaque polyethylene terephthalate film to a wet thickness of 200 μm and then dried at 40° C. for 30 minutes, thereby obtaining a reagent layer.

Preparation of developing layer, processing into assay element and measurement were carried in the same manner as described in Example 1. The results are shown in Table 2.

TABLE 2

| Wavelength | Hemoglobin conc. | | Error |
|---|---|---|---|
| | 0 mg/dl | 300 mg/dl | |
| 500 nm | Δ 0.015 | Δ 0.018 | +20% |
| 525 nm | Δ 0.016 | Δ 0.016 | ±0% |
| 610 nm | Δ 0.017 | Δ 0.014 | −17% |

The results in Tables 1 and 2 show that the measurement error can be reduced to 0% by setting the measuring wavelength to 525 or 585 nm.

Thus, as has been described in the foregoing, the method of the present invention requires no blank test so that additional labor is not necessary and does not cause denaturation on of hemoglobin so that the assay can be handled simply without causing denaturation of the desired component. In addition, the inventive method is accurate in comparison with the prior art method in which the absorbance is measured at a wavelength of 650 nm or more and does not spoil the handiness and simpleness of dry assay elements.

While the invention has been described in detail and with reference to specific embodiments thereof, it will be apparent to one skilled in the art that various changes and modifications can be made therein without departing from the spirit and scope thereof.

What is claimed is:

1. A method for avoiding interference due to hemoglobin caused by chances in the absorption wavelength of hemoglobin over time when light absorption of a color reaction in a test sample is measured in a rate assay, said method comprising the step of carrying out a rate assay where light absorption of a color reaction in a test sample is measured, wherein said rate assay measures activity of an enzyme present in said test sample, wherein said test sample comprises hemoglobin, and wherein said light absorption is measured at a wavelength of from 520 to 526 nm or from 583 to 589 nm.

2. The method of claim 1, wherein said rate assay is carried out using a dry assay element.

3. The method of claim 2, wherein said element comprises a visible coloring agent.

* * * * *